(12) United States Patent
Rodriguez-Emmenegger et al.

(10) Patent No.: US 10,626,209 B2
(45) Date of Patent: Apr. 21, 2020

(54) COPOLYMER OF N-(2-HYDROXYPROPYL) METHACRYLAMIDE AND CARBOXYBETAINE METACRYLAMIDE, POLYMER BRUSHES

(71) Applicants: USTAV MAKROMOLEKULARNI CHEMIE AV CR, V.V.I., Prague—Brevnov (CZ); USTAV FOTONIKY A ELEKTRONIKY AV CR, V.V.I., Prague (CZ)

(72) Inventors: Cesar Rodriguez-Emmenegger, Prague (CZ); Frantisek Surman, Velke Popovice (CZ); Eduard Brynda, Prague (CZ); Tomas Riedel, Prague (CZ); Milan Houska, Prague (CZ); Hana Lisalova, Prague (CZ); Jiri Homola, Prague (CZ)

(73) Assignees: USTAV MAKROMOLEKULARNI CHEMIE AV CR, V.V.I., Brevnov (CZ); USTAV FOTONIKY A ELEKTRONIKY AV CR, V.V.I. (CZ)

( * ) Notice: Subject to any disclaimer, the term of this patent is extended or adjusted under 35 U.S.C. 154(b) by 133 days.

(21) Appl. No.: 15/571,828

(22) PCT Filed: May 5, 2016

(86) PCT No.: PCT/CZ2016/050011
§ 371 (c)(1),
(2) Date: Nov. 4, 2017

(87) PCT Pub. No.: WO2016/177354
PCT Pub. Date: Nov. 10, 2016

(65) Prior Publication Data
US 2018/0346634 A1  Dec. 6, 2018

(30) Foreign Application Priority Data

May 7, 2015  (CZ) .................................. PV2015-313

(51) Int. Cl.
| | | |
|---|---|---|
| *C08F 293/00* | (2006.01) | |
| *C08F 220/56* | (2006.01) | |
| *A61L 27/34* | (2006.01) | |
| *A61L 29/04* | (2006.01) | |
| *A61L 27/50* | (2006.01) | |
| *A61L 33/06* | (2006.01) | |
| *C09D 4/00* | (2006.01) | |
| *A61L 31/10* | (2006.01) | |
| *A61L 29/08* | (2006.01) | |

(Continued)

(52) U.S. Cl.
CPC .......... *C08F 293/005* (2013.01); *A61L 27/34* (2013.01); *A61L 27/50* (2013.01); *A61L 29/04* (2013.01); *A61L 29/085* (2013.01); *A61L 29/14* (2013.01); *A61L 31/10* (2013.01); *A61L 31/14* (2013.01); *A61L 33/064* (2013.01); *C08F 220/56* (2013.01); *C09D 4/00* (2013.01); *C09D 4/06* (2013.01); *C09D 153/00* (2013.01); *C12Q 1/6832* (2013.01); *G01N 33/54393* (2013.01); *G01N 33/56916* (2013.01); *G01N 33/56983* (2013.01); *C08F 2438/03* (2013.01)

(58) Field of Classification Search
CPC ............ C08G 83/001; C08G 2261/128; C08G 2261/136; C08G 2261/1422; C08G 2261/1426; C08G 2261/143; C08G 2261/1432; C08F 20/56; C08F 20/58; C08F 20/60
See application file for complete search history.

(56) References Cited

U.S. PATENT DOCUMENTS

| | | |
|---|---|---|
| 2011/0305898 A1 | 12/2011 | Zhang et al. |
| 2013/0244249 A1 | 9/2013 | Jiang et al. |

(Continued)

FOREIGN PATENT DOCUMENTS

EP     1095711 A2     5/2001

OTHER PUBLICATIONS

International Search Report and Written Opinion of corresponding PCT application No. PCT/CZ2016/050011, dated Nov. 8, 2016.

(Continued)

*Primary Examiner* — Ana L. Woodward
(74) *Attorney, Agent, or Firm* — Notaro, Michalos & Zaccaria P.C.

(57) ABSTRACT

The present invention relates to the preparation and use of copolymers composed of N-(2-hydroxypropyl) methacrylamide (HPMAA) and carboxybetaine methacrylamide (CBMAA).
The invention further describes polymer brushes having structure I S—R-polymer  (I)

wherein S is a substrate;
R is a residue of a polymerization initiator or a RAFT agent bound to the substrate; and "polymer" is the copolymer of N-(2-hydroxypropyl) methacrylamide and carboxybetaine methacrylamide
Furthermore, production of these polymer brushes, containing random or block copolymers grafted to or from a substrate is described.
The copolymer brushes are suitable for protecting substrates from deposition and/or adhesion of biological substances, and/or against thrombus formation. The brushes functionalized by covalent attachment of bioactive substances to CBMAA monomer units are particularly suitable for specific interaction with target biological substances which is not affected by nonspecific deposition of non-target compounds.

9 Claims, 2 Drawing Sheets
Specification includes a Sequence Listing.

(51) Int. Cl.
*A61L 31/14* (2006.01)
*A61L 29/14* (2006.01)
*C09D 4/06* (2006.01)
*C09D 153/00* (2006.01)
*C12Q 1/6832* (2018.01)
*G01N 33/543* (2006.01)
*G01N 33/569* (2006.01)

(56) References Cited

U.S. PATENT DOCUMENTS

2014/0370567 A1   12/2014   Jiang et al.
2015/0056411 A1*  2/2015   Zhang ..................... A61L 27/34
                                                    428/142

OTHER PUBLICATIONS

International Preliminary Examination Report for corresponding PCT application No. PCT/CZ2016/050011, dated Apr. 4, 2017.

* cited by examiner

COPOLYMER OF N-(2-HYDROXYPROPYL) METHACRYLAMIDE AND CARBOXYBETAINE METACRYLAMIDE, POLYMER BRUSHES

FIELD OF ART

The invention relates to a novel copolymer of N-(2-hydroxypropyl) methacrylamide and carboxybetaine methacrylamide.

The invention further relates to polymer brushes that in biological media, such as body fluids, media containing cells, foodstuffs and media from biological productions and from biological media in general, prevent the nonspecific deposition ("fouling") of biological compounds, cells, and microorganisms and, at the same time, allow the attachment of bioactive substances mediating specific interaction of the coating with target components of the biological medium.

Devices, such as bio-sensors, membranes and particles for separation and accumulation of biological substances and cells, drug carriers and diagnostic particles applied into the blood circulation system, blood-contacting devices, and scaffolds for tissue engineering, coated with the polymer brushes are important for many biotechnological and medical applications.

BACKGROUND ART

When any common material comes in contact with a biological medium, the biological matter, particularly proteins, deposit on its surface, this phenomenon is called "fouling". The fouling often deteriorates the function of materials and devices that work in biological media. The problem is especially critical for the materials used in contact with blood serum, plasma, or blood. An effective protection from the fouling is provided by coating the material surface with a layer of an antifouling polymer, such as hydrophilic and electro-neutral poly(oligo(ethylene glycol) methacrylate) (polyHOEGMA), poly(2-hydroxyethyl methacrylate) (polyHEMA), poly(3-hydroxypropyl methacrylate) (polyHPMA), poly(N-(2-hydroxypropyl) methacrylamide) (polyHPMAA), poly(carboxybetaine methacrylate) (polyCBMA), and poly(carboxybetaine acrylamide) (polyCBAA) tethered by one-end to the material surface, the so-called polymer "brush". The brush is prepared by grafting polymer to or from the surface. The "grafting to" technique consists in synthesizing polymer chains with a functional end-group and subsequent anchoring the chains to the surface containing complementary functional groups via covalent bonding, chemisorption, or physisorption. Much better resistance to the fouling is reached by the "grafting from" technique that consists in anchoring an initiator of living radical polymerization, such as atom transfer radical polymerization (ATRP), or an agent of reversible addition fragmentation transfer polymerization (RAFT) to the material surface. After the addition of a polymerization solution containing monomers, the polymer chains grow from the bound residue of the initiator or the RAFT agent (R) by successive addition of monomer units. The "grafted from" brush is usually characterized by the chemical composition determined by reflection IR spectroscopy or XPS and by the thickness measured by ellipsometry or AFM. So far, only the brushes of polyCBMA and polyCBAA grafted from a surfaces have reduced the fouling from undiluted blood plasma below 5 ng/cm$^2$, ("ultra-low fouling") and polyHPMAA brushes have reduced the fouling from blood plasma and other complex biological media below the detection limit of surface plasmon resonance (SPR) biosensors. Bioactive substances can be attached to the polymer brushes by covalent bonding to chemically activated functional groups present in the brush. The functional groups may include carboxyl groups in the zwitterionic betaine side chains of polyCBMA and polyCBAA comprising quarternary ammonium cation and carboxylate anion or hydroxy terminal groups of side chains the other antifouling polymers. Carboxy groups are converted by succinimide/carbodiimide (NHS/EDC) chemistry to active NHS-ester and bioactive substances are subsequently attached via covalent bond of amino groups contained in their structure. The NHS/EDC activation worsens recognizably the antifouling properties of polyCBMA and polyCBAA brushes, while any activation of hydroxyl groups leads to the formation of products that impair significantly the antifouling properties of the other brushes. In many applications, the function of the polymer brush coating consists in selective capturing a target biological compound by specific bioactive (in this case "biorecognition") substances immobilized in the brush. Bioanalytical devices, such as biosensors, designed for direct (so-called "in real-time" or "label-free") detection of analytes are not able to distinguish specific response to the capturing of target analytes from response to nonspecific fouling from the analyzed medium. Thus increasing the number of immobilized biorecognition substances and decreasing the fouling is of great importance for the detection of analytes present at low concentration in complex biological media, particularly in blood plasma and/or serum.

Preparation and activation of the polymer brushes comprising polyCBMA and polyCBAA are disclosed in the documents US20140370567 and US20130244249. The brushes described in these documents do not comprise the copolymer of N-(2-hydroxypropyl) methacrylamide and carboxybetaine methacrylamide.

DISCLOSURE OF THE INVENTION

The present invention relates to copolymers composed of N-(2-hydroxypropyl) methacrylamide (HPMAA) and carboxybetaine methacrylamide (CBMAA), their preparation and use thereof.

The subject of the present invention is a copolymer composed of monomer units of N-(2-hydroxypropyl) methacrylamide (HPMAA) and carboxybetaine methacrylamide (CBMAA) with the molar fraction of CBMAA monomer units in the range of 0.1 to 99.9 mol %, preferably 1 to 70 mol %, or preferably 5 to 60 mol %, or preferably up to 40 mol %, or preferably 10 to 30 mol %.

The copolymer composed of N-(2-hydroxypropyl) methacrylamide (HPMAA) and carboxybetaine methacrylamide (CBMAA) can be, for example, a random copolymer poly(HPMAA-co-CBMAA), or a block copolymer polyHPMAA-b-polyCBMAA.

The copolymer can be prepared using various techniques of living radical polymerization, such as atom transfer radical polymerization (ATRP), single-electron transfer living radical polymerization (SET-LRP), nitroxide-mediated polymerization (NMP), and reversible addition fragmentation transfer polymerization (RAFT). The polymerization techniques, as well as the respective initiators and chain transfer agents, are well known from the literature. The molar fraction of CBMAA monomer units in the random copolymer is adjusted by changing the ratio of CBMAA to HPMAA monomers in the feed and in the block copolymer by the length of polyHPMAA and polyCBMAA blocks.

The present invention further discloses polymer brushes having the structure I:

S—R-polymer      (I)

wherein S is the substrate;
R is the residue of a polymerization initiator or a RAFT agent bound to the substrate; and "polymer" is a copolymer composed of N-(2-hydroxypropyl) methacrylamide (HPMAA) and carboxybetaine methacrylamide (CBMAA).

The polymer layer in the polymer brush has the thickness of 1 nm to 100 nm in the dry state, preferably 5 nm to 50 nm, measured by ellipsometry or AFM method.

The polymer brush may contain the random copolymer (structure II) or the block copolymer (structure III):

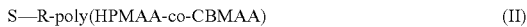
S—R-poly(HPMAA-co-CBMAA)      (II)

S—R-polyHPMAA-b-polyCBMAA      (III).

The polymer brush attached to a substrate may be prepared by the "grafting to" or "grafting from" methods.

The "grafting to" method for the preparation of the random copolymer brush is characterized in that R-poly(HPMAA-co-CBMAA) is polymerized in a solution comprising a mixture of HPMAA and CBMAA monomers and functionalized initiator or RAFT agent. The structure of the functionalized initiator or RAFT agent present in the polymerization solution contains an R moiety capable of binding to complementary functional groups present on the substrate through covalent bonds or strong non covalent adsorption. The copolymer is subsequently attached to the substrate via R.

The "grafting to" method for the preparation of the block copolymer brush is characterized in that R-polyHPMAA is prepared by living radical polymerization in a solution comprising HPMAA monomer and an initiator or a RAFT agent with a functional moiety R, the polymer is isolated and used as a macro-initiator or macrochain-RAFT agent from which the polymerization of the polyCBMAA block proceeds in a solution comprising CBMAA monomer. The resulting di-block copolymer R-polyHPMAA-b-polyCBMAA is subsequently attached to the substrate via R. Alternatively, R-polyHPMAA is prepared by living radical polymerization in a solution comprising HPMAA monomer and an initiator or a RAFT agent with a functional moiety R. The R-polyHPMAA block is attached to the substrate as a macro-initiator or macrochain-RAFT agent from which the block of polyCBMAA is polymerized in a solution comprising CBMAA monomer.

The "grafting from" method for the preparation of the random copolymer brush is characterized in that a polymerization initiator or RAFT agent with a functional moiety R is covalently bound to the substrate surface and subsequently the random copolymer is grafted from the surface in a solution comprising mixture of HPMAA and CBMAA monomers. In one preferred embodiment, the polymerization solution is prepared in water with the addition of ethanol or methanol. The brush typically decreases the fouling below 5 ng/cm$^2$ from biological media, particularly from blood plasma, serum, and other body fluids, and media of biological origin, such as, cell lysates, tissue extracts, cell suspensions, and foodstuff suspensions.

The invention enables a universal modification of various substrates the surface of which contains reactive groups for binding polymerization initiators or RAFT agents. The substrate is made of any material containing functional surface to which the part of initiator or initiator or RAFT agent, R, can be attached through covalent or strong non covalent bonds. The material can contain reactive chemical groups in its structure, reactive groups can be created on the material surface, e.g. by the treatment with oxygen or ammonia plasma, or the material can be coated with a well adhering layer, typically polydopamine autopolymerized on the substrate surface. The shape, proportions, morphology and chemical nature of the substrate can vary widely, the substrate might be a planar object or objects of various shapes, tubes, fibers, particles, membranes, microparticles, nanoparticles, porous materials, metals, silicon, silicate or aluminosilicate based materials (e.g. glass), polymers, inorganic materials, etc. A person skilled in the art is capable of determining a suitable chemistry and suitable initiator or RAFT agent for any selected substrate with no need for an inventive effort. For example, 11-(trichlorsilyl)undecyl-2-brom-2-methylpropanoate ATRP initiator can be attached to glass, silicon with oxidized surface, and a substrate coated with silicone oxide using silane chemistry, RAFT agents trithiocarbonic acid cyano-dimethyl-methyl ester ethyl ester or 2-Cyano-2-propyl benzodithioate and ATRP initiator ω-mercaptoundecyl bromisobutyrate can be attached to silver or gold using thiol chemistry, an initiator bound on a surface of a substrate containing carboxyl groups which can be prepared by incubation with α-brom-isobutyric acid, NHS and EDC, or ATRP initiator 2-brom-2-methylpropanoyl bromide can be attached to a substrate containing amino or hydroxy groups, e.g., substrate coated with a polydopamine layer.

Suitable initiators and suitable types of polymerization for surface grafting are well known to a skilled person, for example atom transfer radical polymerization (ATRP) initiators, single-electron transfer living radical polymerization (SET-LRP) initiators, reversible addition fragmentation transfer polymerization (RAFT) agents. Type of a bond binding the initiator to the substrate depends on the type of the substrate and of the initiator or RAFT agent, however, a skilled person is capable of determining a suitable bonding and suitable initiator or RAFT agent for each substrate with no need of an inventive effort.

Zwitterionic betaine moiety of the CBMAA monomer unit contained in the copolymer comprises quarternary ammonium cation and carboxylate anion. Bioactive substances can be attached to the copolymer using a procedure comprising the transformation of the betaine carboxyl to active ester by reaction with 1-ethyl-3-(3-dimethylaminopropyl)carbodiimide (EDC) and N-hydroxysuccinimide (NHS) or sulfo-NHS and the subsequent reaction of the active ester with amino group contained in the bioactive substance Amino groups are naturally present in protein based bioactive substances, such as antibody and streptavidin and antigen or bioactive substances e.g., DNA probes are synthesized. So far it was believed that active esters, which are not involved in the attachment of bioactive substances, are spontaneously hydrolyzed back to carboxyl anions. Reflection IR spectra indicate that instead of regeneration of carboxylates the active esters are spontaneously deactivated to inert products. This results in a loss of the anti-fouling properties of polyCBMAA and polyCBMAA homopolymer brushes.

The present invention provides a method for optimizing the ratio of the copolymer brush capacity to be functionalized with immobilized bioactive substances to its antifouling properties by adjusting the ratio of CBMAA to HPMAA monomer units. Though the decrease in the content of CBMAA in the copolymer leads to a decrease in the concentration of attached bioactive substances, it considerably decreases the nonspecific fouling. A convenient composition of the copolymer, with regard to keeping the nonfouling properties and the capacity to bind proteins, is 85 mol % of HPMAA and 15 mol % of CBMAA.

In one embodiment, the copolymer brush can be used for passivation of substrates against deposition and/or adhesion of biological media components, in particular molecules and/or cells, and/or against activation of blood coagulation. This use comprises for example passivation of surfaces of devices and materials, whereon undesired deposition upon their contact with biological fluids takes place, such as tubing, fluidic systems, membranes and hollow fibers for dialysis and separation, separation columns, or whereon blood coagulation occurs, for example antithrombotic modifications of blood contacting surfaces in medical devices, such as catheters, blood pumps, oxygenators, membranes and hollow fibers for hemodialysis and hemoperfusion.

Biological media can be in particular body fluids, e.g. blood, coeliolymph, urine, saliva, peritoneal cavity fluid and other media of biological origin, such as blood plasma and serum, cell lysates, tissue extracts, cell suspensions, biological production media and foodstuffs.

In another embodiment, the copolymer brush can be used as an agent for selectively capturing target substances wherein the carboxyl moieties of CBMAA are first activated into reactive intermediates and, subsequently at least one biologically active substance capable of selective capturing the target substance is covalently bound to said reactive intermediates. Biologically active substances can be for example proteins, peptides, nucleic acids, oligonucleotides and other ligands (organic or inorganic). This use encompasses, for example, the production of antifouling surfaces with selective affinity to target substances on bioanalytical devices, particles and membranes for separation and/or accumulation of target substances, carriers for targeted delivery of drugs, genetic information, and diagnostics, and scaffolds for tissue engineering. In one embodiment, particles, membranes, or biomaterials can serve as substrates.

The present invention further comprises biosensors for the direct detection or multi-step detection of analytes, such as SPR sensors or fluorescent sensors, which contain the copolymer brush according to the invention. The substrate is typically the sensor surface. For the direct detection in complex biological media, the content of CBMAA in the random copolymer brush is preferably up to 40 mol %. The composition of 85 mol % of HPMAA and 15 mol % of CBMAA is preferred for the direct detection of analytes in blood plasma, serum, and food extracts.

The present invention further relates to affinity or inert particles coated with the copolymer brush according to the invention, wherein the substrate is the surface of the particle and the copolymer chain layer is attached to said surface. If the particle is porous, the polymer chain layer is typically grafted onto the surface of the pores. Inert particles usually contain non-modified copolymer brush, whereas affinity particles usually contain a polymer brush modified with a bioactive substance.

The present invention further relates to separation membranes comprising the copolymer brush according to the invention. The substrate is typically the surface of a separation membrane and the polymer chain layer is grafted onto the surface of the separation membrane. If the membrane is porous, the polymer chain layer is typically grafted onto the surface of the pores.

EXAMPLES

Example 1

Figure 1:
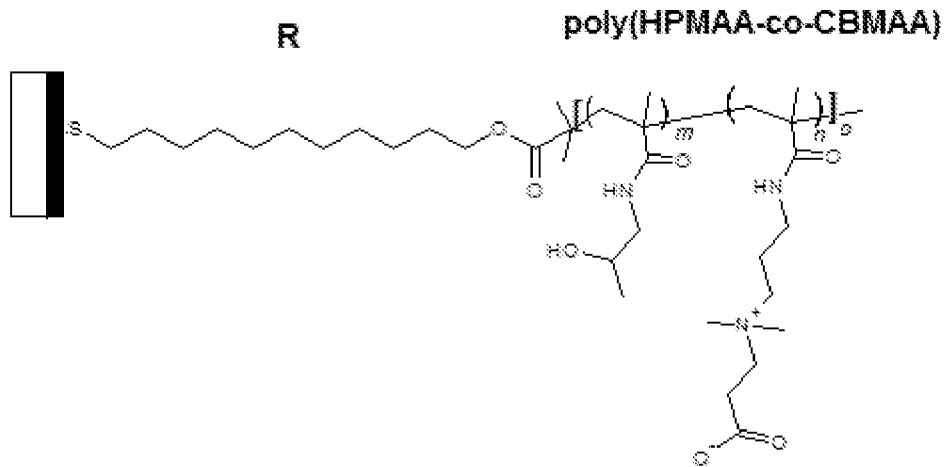
FIG. 1 shows as an example of a polymer brush a statistic copolymer poly(HPMAA-co-CBMAA) grafted from a surface of a golden substrate. R is the residuum of the ATRP initiator ω-merkaptoundecyl bromoisobutyrate covalently bound to the golden surface, m is the number of HPMAA monomeric units, and n is the number of CBMAA monomeric units randomly distributed in the copolymer, o is the number of all monomeric units in the polymer chain.

Preparation of Poly(HPMAA-co-CBMAA) by RAFT Polymerization in Solution

In a Schlenk flask equipped with magnetic stirrer bar, monomers N-(2-hydroxypropyl) methacrylamide (HPMAA, 4.3 g, 30 mM, 85 mol %), carboxybetaine methacrylamide (CBMAA, 1.3 g, 5.2 mM, 15 mol %) and chain transfer agent 4-Cyano-4-(phenylcarbonothioylthio)pentanoic acid (CTP, 35 mg, 0.124 mM) were dissolved in 45 ml of DMAc and deoxygenated by four freeze-pump-thaw cycles. Subsequently, 1 ml (0.051 mM) of the initiator 2,2'-Azobis[2-(2-imidazolin-2-yl)propane]dihydrochloride solution (VA-044, 16.4 mg, 1 ml DMAc) was added and another one freeze-pump-thaw cycle was performed. The flask containing the pink solution was filled with argon and placed into the oil bath (50° C.) to start the polymerization. After 24 h, the polymerization was quenched by exposing the reaction mixture to air and liquid nitrogen. The polymerization solution was dialyzed against deionized water for 46 h using a SpectraPor 3 membrane (MWCO 3500 Da) and freeze-dried to yield a pink solid. The conversion was 80% as determined from $^1$H NMR spectroscopy. The obtained polymer was characterized by SEC $M_n$=66000 g·mol$^{-1}$, Đ=1.35.

Example 2

Preparation of PolyHPMAA-b-polyCBMAA by RAFT Polymerization in Solution

Preparation of the first block polyHPMAA as a macro-RAFT agent: In a Schlenk flask equipped with magnetic stirrer bar, HPMAA monomer (3.1 g, 21.7 mM), CTP (50 mg, 0.178 mM) were dissolved in 17.8 ml of DMAc and deoxygenated by four freeze-pump-thaw cycles. Subsequently, 100 µl (0.357 mM) of the initiator V-501 solution (100 mg, 1 ml DMAc) was added and another one freeze-pump-thaw cycle was performed. The flask containing the pink solution was filled with argon and placed into the oil bath (70° C.) to start the polymerization. After 8 h, the polymerization was quenched by exposing the reaction mixture to air and liquid nitrogen. The polymerization solution was dialyzed against deionized water for 46 h using a SpectraPor 3 membrane (MWCO 3500 Da) and freeze-dried to yield a pink solid. The conversion was 38% as determined from $^1$H NMR spectroscopy. The obtained polymer was characterized by SEC $M_n$=6500 g·mol$^{-1}$, Đ=1.1.

The preparation of second block and the extension of polyHPMAA macroRAFT agent to polyHPMAA-b-poly-CBMAA was performed as follows. The above noted polyHPMAA ($M_n$=6500 g mol$^{-1}$, Đ=1.1) was employed as a macroRAFT agent. In a Schlenk flask equipped with magnetic stirrer bar, 125 mg (~0.019 mM) of polyHPMAA was dissolved in 4 ml of acetate buffer. Then, CBMAA monomer (690 mg, 2.8 mmol) was added and the mixture deoxygenated by four freeze-pump-thaw cycles. Subsequently, 100 µl (0.004 mM) of the initiator V-501 solution (10 mg, 1 ml acetate buffer) was added and another one freeze-pump-thaw cycle was performed. The polymerization mixture was allowed to polymerize for 6 h. After that, the polymerization was quenched by exposing the reaction mixture to air and liquid nitrogen. The polymerization solution was dialyzed against deionized water for 72 h using a SpectraPor 3 membrane (MWCO 3500 Da) and freeze-dried to yield a pink solid. The conversion was 63% as determined from $^1$H NMR spectroscopy. The obtained polymer was characterized by SEC $M_n$=35 000 g·mol$^{-1}$, Đ=1.2.

Example 3

Preparation of Poly(HPMAA-co-CBMAA) Brush by "Grafting to" Gold

The copolymer poly(HPMAA-co-CBMAA), $M_n$=66 000 g·mol$^{-1}$, Đ=1.35 was prepared by RAFT polymerization according to the Example 1. The procedure lead to the copolymer terminated with dithiobenzoate functional group (DTB) which was a residue of chain transfer agent 4-Cyano-4-(phenylcarbonothioylthio)pentanoic acid used for the RAFT polymetization. Gold-coated glass substrate was rinsed twice with ethanol and deionized Milli-Q water, blow-dried with nitrogen, and cleaned in a UV/Ozone cleaner for 20 min. For the copolymer grafting to gold surface poly(HPMAA-co-CBMAA)-DTB was dissolved in dimethylformamide (DMF) 3.5 ml and subsequently 2 ml of dichloroethane (DCE) was dropped until cloudy solution appeared at the final DMF/DCE volume ratio of 65/35%. Immediately after cleaning, the substrate was immersed in the solution of poly(HPMAA-co-CBMAA)-DTB (100 mg in 5.5 ml of DMF/DCE). After 4 days in dark, the substrate was taken out of the solution, washed successively with DMF and water and stored in water.

Example 4

Preparation of Poly(HPMAA-co-CBMAA) Brush by "Grafting from" Gold

Figure 2:
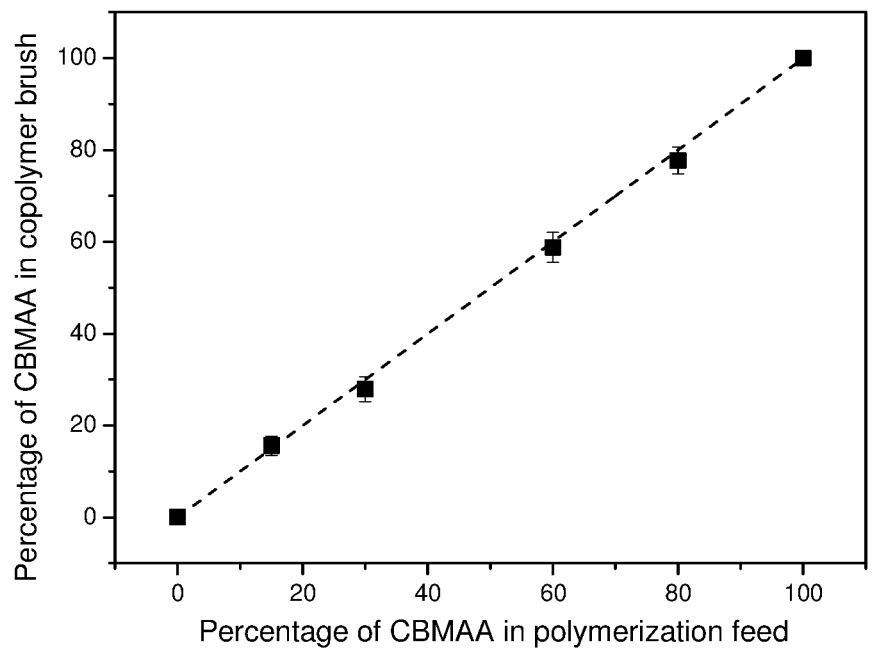
FIG. 2 shows the dependence of the percentage of CBMAA monomeric units in the brush of poly(HPMAA-co-CBMAA) on the percentage of CBMAA monomer in the mixture of HPMAA and CBMAA monomers present in the polymerization solution. The copolymer was grafted from the golden surface of the SPR chip by ATRP according to the Example 4 from the polymerization solutions containing various concentrations of CBMAA to HPMAA monomers.
Figure 3:
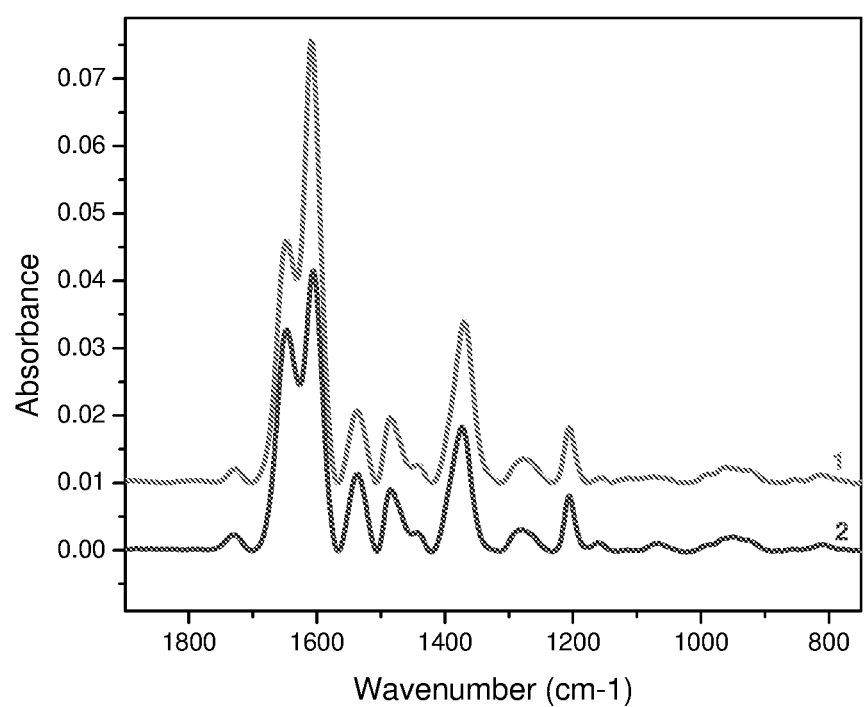
FIG. 3 shows the decrease in concentration of ionized carboxyl groups (the intensity of the band of valence vibration C=O at 1607 cm$^{-1}$) in the polyCBMAA brush grafted from SPR chip after the NHS/EDC activation measured by FTIR GASR spectroscopy (Example 9). (1) polyCBMAA; (2) polyCBMAA, NHS/EDC activation (12 min), PBS (60 min).

A glass plate was coated with a gold layer in vacuum. The plate was rinsed with ethanol and water, dried, and cleaned 20 min in UV/Ozone cleaner. The plate was immersed into the 0.1 M solution of initiator ω-merkaptoundecyl bromoisobutyrate in ethanol for 24 h in dark. Into the Schlenk flask containing CuCl (35 mg), CuCl$_2$ (10.5 mg) and Me$_4$Cyclam (121 mg) 7 ml of de-gassed methanol was added and the catalytic mixture was mixed until fully dissolved. In another Schlenk flask 3.1 g of the monomer mixture containing 15 mol % CBMAA and 85 mol % HPMAA was dissolved, while cooled with ice, in 12 ml of de-gassed water and 5 ml of ethanol. After dissolution, the catalyst solution was added to the flask under argon. Homogeneous polymerization mixture was dosed under argon into the second Schlenk flask with an inserted plate coated with the initiator and the mixture was polymerized for 120 min at 30° C. Then the plate was rinsed with water. The same procedure was used to prepare the brushes in solutions comprising mixtures of CBMAA and HPMAA monomers at molar ratios of CBMAA to HPMA of 7:93, 3:7, 3:2, and 4:1. The molar ratios of CBMAA to HPMA in the copolymer brushes as determined by FTIR-GASR spectroscopy were similar as those in the polymerization feed (see FIG. 2) indicating a random character of the copolymerization. The thickness of the surface polymer layer determined by ellipsometry was 30 nm.

Example 5

Preparation of Poly(HPMAA-co-CBMAA) Brush by "Grafting from" Glass

A glass plate was rinsed with ethanol and water, dried, and finally cleaned 20 min in UV ozone cleaner. The plate was immersed for 3 h to 1 mM solution of initiator 11-(trichlorsilyl)undecyl-2-bromo-2-methylpropanoate in dry toluene. After that, the plate was rinsed with toluene, acetone, ethanol, and water, and dried. 7 ml of de-gassed methanol was added into a Schlenk flask containing CuCl (35 mg), CuCl$_2$ (10.5 mg) and Me$_4$Cyclam (121 mg) and the catalytic mixture was mixed until fully dissolved. In the second Schlenk flask 2.9 g of the monomer mixture containing 15 mol % CBMAA and 93 mol % HPMAA was dissolved, while cooled with ice, in 12 ml of de-gassed water and 5 ml of ethanol. After that the catalyst solution was added to the flask under argon The polymerization mixture was added under argon into the third Schlenk flask containing the plate coated with the initiator, and the grafting of the copolymer was performed for 120 min at 30° C. Then, the plate was rinsed with water.

Example 6

Preparation of Poly(HPMAA-co-CBMAA) Brush by "Grafting from" Nano-Particles (NP) of ε-Polycaprolactone (PCL)

The solution of α-bromo isobutyric acid, 0.15 M, N-hydroxysuccinimide (NHS), 0.05 M, and EDC, 0.2 M, in water was left 7 min at 25° C. and then transferred to suspension of hollow poly(ε-caprolactone) nano-particles (diameter 150 nm, 5.5×10$^9$/ml), and the suspension was mixed through the night. Then the suspension was dialyzed 12 h at the room temperature through the membrane Spectra/Pore® (6 000 through 8 000 Da). CuBr$_2$ (8.1 mg), 2,2'-dipyridyl (145 mg) and 5.7 g of the monomer mixture containing 15 mol % CBMAA and 85 mol % HPMAA was dissolved, while cooled with ice, in 10 ml of water was degassed by bubbling argon for 1 h. Then CuCl (37 mg) was added under argon and the solution was bubbled with argon for further 30 min. This solution was added to 5 ml of suspension of nano-particles with the bound initiator, and the system was polymerized under argon at 30° C. The size distribution of nano-particles before and after modification was determined using the method of quasi-elastic dispersion. The thickness of the polymer brush was controlled by the polymerization time (30 min to 150 min) in the range from 20 nm to 200 nm. The coverage of nano-particles with the poly(HPMAA-co-CBMAA/15 mol %) brush prevented the aggregation of nano-particles upon incubation with undiluted blood plasma.

Example 7

Preparation of Poly(HPMAA-co-CBMAA) Brush by "Grafting from" Silicon Coated with Anchoring Intermediate Layer of Polydopamine (PDA)

A silicon plate was cleaned by sonication in methanol and water, immersed for 10 min in the mixture of 25% ammonia, 30% hydrogen peroxide, and water (1:1:5, v/v/v) heated to 70° C. Then it was rinsed with water and ethanol, dried and cleaned 2 h in the UV/Ozone cleaner. Then the plate was inserted into the opened Petri dish containing the solution of 2 mg of dopamine hydrochloride per ml of air saturated 10 mM Tris-HCl buffer, pH 8.5. After 3 h of gentle mixing, the plate was rinsed with water, sonicated in water 15 min and dried. The plate with the layer of PDA (13 nm) was immersed into the solution of 0.24 M triethylamine at 0° C., put into the shaker and the solution of 2-brom-2-methylpropanoyl bromide (0.24 M in 10 ml of tetrahydrofuran) was added at 0° C. After 3 min, the plate was removed and rinsed successively with tetrahydrofuran, ethanol, and water, and dried. Degassed ethanol (30 ml) was transferred under argon into the Schlenk flask containing CuBr (57.3 mg), CuBr$_2$ (17.7 mg) and Me$_4$Cyclam (122.7 mg). The blue solution of this catalyzer was transferred to the second Schlenk flask containing 4.5 g of the monomer mixture of CBMAA (15 mol %) and HPMAA (85 mol %). The polymerization solution was transferred to the reactor containing the silicone plate coated with the anchoring layer of polydopamine, and left to polymerize 2 h at 30° C. The plates were then rinsed with ethanol and water. The presence of polymer brush of poly(HPMAA-co-CBMAA/15 mol %) was checked by FTIR-IRRAS spectroscopy and the thickness of the layer determined by ellipsometry was 20 nm.

Example 8

Antithrombogenic Characteristics of Poly(HPMAA-co-CBMAA/15 mol %)

The surface of a glass plate coated with poly(HPMAA-co-CBMAA/15 mol %) brush according to the Example 5 was immersed in the citrated blood plasma from a healthy donor mixed with 1M solution of CaCl$_2$ in water. The turbidity was measured at 405 nm. In comparison with untreated glass, the re-calcification time was extended 8-times (40 min vs. 5 min). Thrombogenicity of this surface was further assessed by monitoring of coagulation kinetics of whole blood. Whole blood from a healthy donor collected into citrate was mixed with a 1 M solution of CaCl$_2$ in water (final concentration 0.02 M) and immediately applied to the surface of the sample (100 μl). At time intervals of 5, 15 and 30 min, the blood coagulation was stopped by adding 3 ml of distilled water. After 5 min, 200 ml of the sample was collected and the amount of released hemoglobin from erythrocytes not caught in the blood clot was determined from absorbance at 540 nm. The size of the blood clot is inversely proportional to the absorbance value. While on the surface prepared according to the Example 2, there was no significant decrease in hemoglobin levels even after 30 min, on the untreated glass surface the decrease occurred already after 5 min, and after 30 min more than 85% of erythrocytes were captured in the blood clot.

Example 9

Binding of Biorecognition Substances to Poly(HPMAA-co-CBMAA) Brushes Grafted from SPR Chips The brushes of poly(HPMAA-co-CBMAA) copolymers containing 7 mol %, 15 mol % and 30 mol % of CBMAA, and the brushes of polyCBMAA and polyHPMAA homopolymers were grafted from gold surface of SPR chips using the procedure described in the Example 4. SPR chips coated with the polymer brush were rinsed with water, 10% acetic acid, water, nitrogen blow dried, and inserted into a flow cell of the SPR sensor instrument. Then they were activated in situ for 20 min with the solution of NHS, 0.1 M, and EDC, 0.05 M, in water. The solution was replaced with borate buffer, 10 mM, pH 8.5, and after 15 min the activated chips were reacted with a solution of a biorecognition substance (antibody against *E. coli*, 50 μg anti-*E. coli*/ml, 100 μg streptavidin/ml in the borate buffer, or amino-modified oligonucleotide probe, 11-mer, 4 μM). The functionalized chips were sequentially rinsed with borate buffer (10 mM, pH 8.5, 50 min) containing 150 mM NaCl and 10 mM imidazole, NaOH (2 mM, 3 min) and ethanolamine (1 M, 5 min). Finally, the chips were rinsed with water and the amount of immobilized ligand was determined by SPR.

TABLE 1

The amount of the bound antibody anti-*E. coli*, streptavidin, and amino-modified oligonucleotide probe on polyCBAA, poly(HPMAA-co-CBMAA), polyHPMAA, and polyCBMAA.

| Polymer brush | Bound ligand [ng/cm$^2$] | | |
|---|---|---|---|
| | Anti-*E. coli* | Streptavidin | ON-probe |
| polyCBAA* | 153.2. | 136.8 | 30.9 |
| polyHPMAA | 0.0 | 0.0 | N/A |
| Poly(HPMAA-co-CBMAA/7 mol %) | 20.6 | N/A | 2.9 |
| Poly(HPMAA-co-CBMAA/15 mol %) | 200.1 | 30.1 | 18.6 |
| Poly(HPMAA-co-CBMAA/30 mol %) | 362.2 | 60.8 | 30.6 |
| PolyCBMAA | 450.8 | 242.0 | 31.5 |

*Delivered from the University of Washington, Seattle, USA

Table 1 demonstrates the dependence of the binding capacity for ligands on the content of CBMAA in the copolymer

Example 10

Binding of Surface Antigen of Hepatitis B (HBsAg) Virus to Poly(HPMAA-co-CBMAA) Brush Grafted from SPR Chip Poly(HPMAA-co-CBMAA/15 mol %) brush grafted from the SPR chip according to the Example 4 was activated for 10 min by water solution of EDC, 0.2 M, and NHS, 0.05 M. Then the surface was rinsed shortly with acetate buffer (10 mM, pH 5) and HEPES buffer (10 mM, pH 7.5) and the solution of 25 μg HBsAg/ml HEPES was added. The mixture was allowed to react for 10 min and then the plate was transferred to PBS buffer. The SPR chip prepared by such procedure was used for the direct detection of antibodies to the hepatitis B virus in sera of patients diluted with PBS to 10%. Positive and negative sera of patients were resolved and the relative titer of antibodies against the hepatitis B virus was determined.

The fluorescent biosensor with the bound HBsAg prepared by the same procedure and combined with a fluorescently labeled secondary antibody was used for the detection of anti-HBsAg in saliva samples by SPR enhanced fluorescence. The limits of detection of this method achieved 10 pM in this model example.

Example 11

Resistance of Poly(HPMAA-co-CBMAA) Brushes to Non-Specific Fouling from Blood Plasma and Foodstuffs Before and After Binding Biorecognition Substances Brushes of poly(HPMAA-co-CBMAA) copolymers containing 7 mol %, 15 mol % and 30 mol % of CBMAA, and brushes of polyCBMAA and polyHPMAA were grafted from the gold surface of SPR chips using the procedure described in Example 4 and functionalized by attachment of antibody against $E.\ coli$ (anti-$E.\ coli$) according to Example 9 (see Table 1 for the amount of the attached antibody). The surfaces coated with the brushes without the attached anti-$E.\ coli$ and the surfaces after the functionalization were exposed to undiluted citrate blood plasma and undiluted extracts of the foodstuffs for 10 min at 25° C. The fouling was determined by SPR (Table 2).

Table 2 documents that the excellent antifouling properties of polyHPMAA brush are not affected when exposed to the conditions of the functionalization. The fouling remained below the limit of detection of the SPR method (0.3 ng/cm$^2$) in all the tested media.

Example 12

SPR Detection of Pathogenic Bacteria in Food Samples Using Poly(HPMAA-co-CBMAA) Brush Grafted from SPR Chip Pathogenic bacteria $E.\ coli$ $O$157:H7 (deactivated with heat shock) in the buffer solution and 100% extract from hamburger and lettuce were detected using SPR four-channel sensor. SPR chip covered with poly(HPMAA-co-CBMAA/15 mol %) and functionalized with the respective antibodies (channel 1-3:anti-$E\ coli$, channel 4: anti-Salm) were prepared according to the Example 9. The amounts of the immobilized antibodies were ~244 ng/cm$^2$ for anti-$E.\ coli$ (channel 1-3) and ~204 ng/cm$^2$ in the reference channel with immobilized antibody to $Salmonella$ spp., anti-Salm (channel 4). The detection of bacteria was performed in three steps. In the direct detection step I the bacteria $E.\ coli$ O157:H7 at the concentration of 1.5×10$^7$ cfu/ml were detected in PBS buffer (channel 1), in the extract from hamburger (channel 2) and in the extract from lettuce (channels 3 and 4). The time of incubation was 10 min at the flow of 30 µl/min and then the sensor was rinsed 10 min with PBS. In the step II, the secondary biotinylated antibody to $E.\ coli$ (5 µg/ml) was circulated in all channels for 15 min to confirm specificity of the binding of the bacteria to immobilized antibodies. In the Step III, streptavidin (100 µg/ml,) was circulated for 15 min to increase the response of the sensor. The shifts of the resonance wavelength displayed for each step separately are shown in Table 3.

TABLE 2

Fouling from undiluted blood plasma and undiluted food extracts. A - Unmodified brushes; B - Brushes functionalized with anti-$E.\ coli$.

| | Fouling [ng/cm$^2$] | | | | | |
|---|---|---|---|---|---|---|
| | Blood plasma | Milk | Spinach | Cucumber | Hamburger | Salad |
| A - Non-functionalized surfaces | | | | | | |
| PolyCBAA* | 6.8 | 0.0 | 4.8 | 0.0 | 0.0 | 0.0 |
| PolyHPMAA | 0.0 | 0.0 | 0.0 | 0.0 | N/A | 0.0 |
| Poly (HPMAA-co-CBMAA/ 7 mol %) | 0.0 | 0.0 | 0.0 | 0.0 | N/A | 0.0 |
| Poly(HPMAA-co-CBMAA/ 15 mol %) | 2.9 | 0.0 | 0.5 | 0.3 | 0.0 | 0.2 |
| Poly(HPMAA-co-CBMAA/ 30 mol %) | 10.0 | 0.6 | 1.2 | 1.4 | 0.0 | 1.4 |
| PolyCBMAA | 11.1 | 27.9 | 2.7 | 2.1 | N/A | 2.4 |
| B. Functionalized surfaces | | | | | | |
| PolyCBAA* | 20.2 | 8.0 | 62.9 | 8.1 | 2.2 | 4.3 |
| PolyHPMAA | 0.0 | 0.0 | 0.0 | 0.0 | N/A | 0.0 |
| Poly (HPMAA-co-CBMAA/ 7 mol %) | 2.6 | 0.0 | N/A | 0.0 | N/A | 0.0 |
| Poly(HPMAA-co-CBMAA/ 15 mol %) | 8.5 | 1.7 | 3.4 | 0.0 | 0.0 | 0.0 |
| Poly(HPMAA-co-CBMAA/ 30 mol %) | 16.2 | 6.8 | 4.2 | 2.8 | N/A | 3.5 |
| PolyCBMAA | 25.4 | 30.5 | 12.2 | 3.4 | N/A | 4.9 |

*Delivered from the University of Washington, Seattle, USA

TABLE 3

Responses of the sensor (shift of the resonance wavelength in nm) upon detection of
E. coli O157:H7 to poly(HPMAA-co-CBMAA/15%) in Steps I., II., and III. Channels 1-3
(measuring) were functionalized anti-E. coli, channel 4: reference anti-Salm.

| | Response of SPR sensor [nm] | | | |
|---|---|---|---|---|
| Detection step | Channel 1 - anti-E. coli/ detection in PBS | Channel 2 - anti-E. coli/detection in extract from hamburger | Channel 3 - anti-E. coli/detection in extract from lettuce | Channel 4 (ref.) - anti-Salm/detection in PBS |
| I. Direct detection of E. coli O157:H7 | 0.8 | 1.1 | 0.9 | 0.0 |
| II. Detection of biotinylated antibody anti-Ecoli | 5.5 | 5.6 | 6.3 | 0.0 |
| III. Detection of streptavidin | 11.1 | 11.5 | 12.0 | 0.1 |

Example 13

SPR Detection of MicroRNA Using Poly(HPMAA-co-CBMAA/15 mol %) Brush Grafted from SPR Chip SPR chips were coated with poly(HPMAA-co-CBMAA/15 mol %) brush (thickness about 40 nm in hydrated condition) and functionalized by the covalent attachment of amino-modified oligonucleotide probes using the optimized NHS/EDC chemistry (probe—NdmiR-122, sequence 5'-Am-MC12-CA AAC ACC ATT G-3', 4 µM in 10 mM borate buffer, pH 8.0, 30 min, flow 7.5 µl/min, 25° C.) according to the Example 9. MicroRNA (miR-122) was detected by the biosensor at the concentration of 100 nM in PBS. To regenerate the biosensing surface, the captured miRNA molecules were released from the immobilized oligonucleotide probes by NaOH (6 mM, 5 min) and the measurement was repeated after re-injecting the miRNA solution, The sensor response did not change significantly, even after four measuring/regeneration cycles.

Example 14

SPR Detection of DNA Oligonucleotides Using Poly(HPMAA-co-CBMAA/15 mol %) and PolyCBMAA Brushes Grafted from SPR Chip SPR chips were coated with poly(HPMAA-co-CBMAA/15 mol %) or polyCBAA brushes and functionalized by the covalent attachment of streptavidin using NHS/EDC chemistry (50 µg/ml of streptavidin in 10 mM borate buffer, pH 8.0, 20 min, flow 20 µl/min, 25° C.) according to the Example 9. The biotinylated oligonucleotide probes were bound to the immobilized streptavidin through noncovalent streptavidin-biotin interaction in solution of the probe (200 nM in PBS) The number of probes bound to one molecule of streptavidin was set at an average value of 3.1 for the surface with poly(HPMAA-co-CBMAA/15 mol %) and 3.2 for polyCBAA. A response of the biosensor was detected after injecting solution of target DNA oligonucleotides (200 nM in PBS, 15 min, 30 ml/min, 25° C.). An average number of the captured DNA oligonucleotide per one immobilized probe was 0.9 on poly(HPMAA-co-CBMAA/15 mol %) and 0.8 on polyCBAA.

The invention claimed is:

1. A substrate with a polymer brush having the structure I:

$$S—R\text{-polymer} \quad (I)$$

wherein S is a substrate;
R is a residue of a polymerization initiator or a RAFT agent bound to the substrate; and
"polymer" is a copolymer of N-(2-hydroxypropyl) methacrylamide and carboxybetaine methacrylamide,
wherein the molar fraction of carboxybetaine methacrylamide monomer units is up to 40 mol %.

2. The substrate with the polymer brush according to claim 1, which is selected from polymer brush containing a random copolymer of N-(2-hydroxypropyl) methacrylamide (HPMAA) and carboxybetaine methacrylamide (CBMAA) of structure II:

$$S—R\text{-poly(HPMAA-co-CBMAA)} \quad (II),$$

or a block copolymer composed of a poly(N-(2-hydroxypropyl) methacrylamide) block (polyHPMAA) and a poly(carboxybetaine methacrylamide) block (polyCBMAA) of structure III:

$$S—R\text{-polyHPMAA-b-polyCBMAA} \quad (III).$$

3. The substrate with the polymer brush according to claim 1 wherein the copolymer in a dry state has a thickness of 1 nm to 100 nm.

4. A method for preparation of the substrate with the polymer brush according to claim 2 wherein the copolymer of N-(2-hydroxypropyl) methacrylamide and carboxybetaine methacrylamide is a random copolymer, characterized in that R-poly(HPMAA-co-CBMAA) is prepared by living radical polymerization in a solution comprising mixture of HPMAA and CBMAA monomers, polymerization initiator or a RAFT agent with a functional moiety R, and the R-poly(HPMAA-co-CBMAA) is subsequently attached to the substrate via R.

5. A method for preparation of the substrate with the polymer brush according to claim 2, wherein the copolymer of N-(2-hydroxypropyl) methacrylamide and carboxybetaine methacrylamide is a random copolymer, characterized in that a polymerization initiator or RAFT agent with a functional moiety R is covalently bound to a substrate surface and subsequently random copolymer of N-(2-hydroxypropyl) methacrylamide and carboxybetaine methacrylamide is grafted from the surface in a solution comprising mixture of HPMAA and CBMAA monomers.

6. A method for preparation of the substrate with the polymer brush according to claim 2 wherein the copolymer of N-(2-hydroxypropyl) methacrylamide and carboxybetaine methacrylamide is a block copolymer, characterized in that a polymerization initiator or RAFT agent with a functional moiety R is covalently bound to a substrate surface, then the block copolymer of polyHPMAA-b-polyCBMAA is polymerized from the surface in a solution comprising HPMAA monomer and in a solution comprising CBMAA monomer, respectively.

7. The substrate with the polymer brush according to claim 1, wherein the molar fraction of carboxybetaine methacrylamide monomer units is up to 30 mol %.

8. A bioanalytical device comprising the polymer brush according to claim 1,
  wherein the device surface is the substrate S of the polymer brush.

9. The bioanalytical device of claim 8, wherein the device is a sensor for direct detection of analytes or sensor for multi-step detection of analytes.

* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial
<220> FEATURE:
<223> OTHER INFORMATION: Example 13 - probe sequence

<400> SEQUENCE: 1
caaacaccat tg                                                          12
```